United States Patent [19]

Sikter

[11] Patent Number: 5,348,749
[45] Date of Patent: Sep. 20, 1994

[54] METHOD FOR TREATING PANIC DISORDER

[75] Inventor: Andras Sikter, Budapest, Hungary

[73] Assignee: S+V Engineering Kft., Budapest, Hungary

[21] Appl. No.: 972,322

[22] Filed: Nov. 5, 1992

[30] Foreign Application Priority Data

May 10, 1990 [HU] Hungary ............................ 2980/90

[51] Int. Cl.⁵ .............................................. A61K 33/42
[52] U.S. Cl. .............................................. 424/604
[58] Field of Search ................ 424/601, 604; 514/494, 514/561

[56] References Cited

U.S. PATENT DOCUMENTS

| | | | |
|---|---|---|---|
| 4,582,709 | 4/1986 | Peters et al. | 424/604 |
| 4,725,427 | 2/1988 | Ashmead et al. | 514/494 |
| 4,753,804 | 6/1988 | Iaccheri et al. | 424/491 |
| 4,871,550 | 10/1989 | Millman | 424/601 |

FOREIGN PATENT DOCUMENTS

| | | |
|---|---|---|
| 307620 | 5/1973 | Austria . |
| 0048473 | 3/1982 | European Pat. Off. . |
| 0053244 | 6/1982 | European Pat. Off. . |
| 0223762 | 5/1987 | European Pat. Off. . |
| 0245669 | 11/1987 | European Pat. Off. . |
| 0326826 | 8/1989 | European Pat. Off. . |

OTHER PUBLICATIONS

B. Helwig et al., "Salviamin ® OP", p. 389 (1989).
H. Helwig et al., vol. 1, Sixth Edition, pp. 24–3, vol. II, 35–20, 35–21, and 39–17, Oct. 1988.

*Primary Examiner*—Raymond J. Henley, III
*Attorney, Agent, or Firm*—Young & Thompson

[57] ABSTRACT

A method for treating panic disorder, which comprises administering to a human suffering from panic disorder 0.03 to 1.5 mmoles of zinc and 2 to 100 mmoles of magnesium and 2 to 60 mmoles of phosphorus and 3 to 90 mmoles of potassium as a daily dose in a composition consisting essentially of zinc, magnesium, phosphorus and potassium, in a weight ratio of 1–15:25–200:-50–200:100–500, respectively.

1 Claim, No Drawings

METHOD FOR TREATING PANIC DISORDER

This application is a continuation-in-part of co-pending international application No. PCT/HU91/00018 filed May 10, 1991, which designates the United States.

TECHNICAL FIELD

The invention relates to a method for treating panic disorder in humans, by administration of a novel pharmaceutical composition comprising zinc, magnesium, phosphorus and potassium in a determined ratio.

BACKGROUND ART

It is known that mineral substances and trace elements are of vital importance in the human (generally in living) organism(s). A great number of publications deal with the effect of the given elements (such as zinc, potassium, magnesium and phosphorus) applied separately.

The idea of the "milieu interieur" created by Claude Bernard in last century is also known. According to Dr. Bernard the main condition of free and independent life is the stability in the interior milieu. The mechanism ensuring the permanence in the "interior milieu" is very important for life. The question of "milieu interieur" is still under dispute, however, it is accepted by every scientist that the extracellular and intracellular ion concentrations are a part of it.

The second main thermodinamical law is an universal rule, so it must be valid in case of living organisms as well.

Living organisms (living cells) do not seem to come under this rule as they keep themselves at an energy level higher than that of their environment. Of course this is just a semblance, the cells are unable to uphold this higher energy level on the long run, that is why they get old, sick and die.

Having studied numerous publications I came to the recognition that in old or sick cells the concentration of adenosine triphosphate (ATP), carrying the biological energy is decreasing, or at least the maximal amount of ATP which can be formed during a certain period of time is lower, thus the maximal efficiency of the cell is decreased. In close connection with this fact the intracellular ion concentration of the patient is changed, which can be both cause and effect. The trend of this change in the ion concentration can be predicted in a high probably (surely because of the fact that some ions are kept within the cell and others are kept off the cytoplasm by consuming biological energy, mainly ATP).

The original ion milieu seems to be optimal, any change in it exerts a negative effect on the cellular metabolism, and consequently on ATP production as well, which results in a further damage in the ion milieu of the cell, thus a particular self-inducing circle is developed.

As a rule this process does not go the end, i.e. to necrocytosis, but the metabolism and the ion milieu of the cell usually are stabilized at a lower level. This is valid, first of all, for the actually sick groups, tissues or organs, but it can be followed by secondary and tertiary alterations and the defensive mechanisms of the organism may simultaneously be activated.

I found that in the sick cells the concentration of the following ions tend to increase: sodium, calcium, hydrogen, chloride and copper. At the same time the concentration of the following ions probably decreases in the sick cells: potassium, magnesium, zinc, monohydrophosphate and dihydrophoshpate.

This whole concept is just a hypothesis, since the existence of ion pumps, working with biological energy (ATP) is proved and accepted only in case of three of the above ions (sodium, potassium and calcium). As to the rest of the ions the data available are few (as to di- and monohydrophosphate ions) or contradictory (as to zinc ion), or there are no data at all (as to chloride, hydrogen or Cu ions), or they support an opposite view (e.g. in the case of magnesium ions an active transport in the opposite direction is supposed, [see Hoang, N. D.: Magnesium Bulleting, 11 159-165 (1989)]. However, the reality of my concept is proved by good results of the clinical experiments.

Several works have recently been published regarding the physiological and pathological effect of magnesium and zinc. Rasmussen H. S. [Clin. Cardiol. 11 377-381 (1988)] applied with success magnesium salts in the form of i.v. infusions in a dose above the physiological level for treating acute myocardial infraction. Others have used magnesium salt i.v. in a dose close to the toxical level for treating arrhythmia [Iseri, L. T. et al: Magnesium 8, 299-306 (1989)].

Rasmussen, H. S. et al [Clin. Cardiol. 11 377-381 (1988)] have found that the i.v. application of magnesium in large doses has a long-lasting positive effect. This is due to the fact, I think, that magnesium had a normalizing effect on the sick cells, i.e. it promoted regeneration. Probably this is also an ion supplementation, however, it could be (partially) achieved only with very large serum doses.

Other researchers consider the use of magnesium in a physiological dose to be favourable, e.g. in case of hypertonia (magnesium aspartate containing 200 mg of magnesium daily). In this dose the results are moderate or even doubtful. It is generally accepted at the same time, that the majority of the civilized nations is underfed with magnesium, thus the application of magnesium product is not harmful, but definitely desirable also for healthy people.

As regards zinc the experiences are similar. It has been used as dermacological agent for centuries, however, it met real success only after its new discovery [Prasad, A. S. et al: J. Lab. Clin. Med. 61, 537-549 (1963)]. This had been preceded by the publication of Vallee's standard work about the per os use of zinc for treating liver cirrhosis [Vallee, B. L.: N. Engl. J. Med. 257, 1055-1065 (1957)].

Although zinc is used nowadays for treating 25 difference diseases in a dose exceeding the physiological level 6-8 times, its use is not widespread in medical practice.

The lack of potassium caused by diuretics and other agents is generally known and accepted, just like the fact that this lack must be ceased. It is believed that the lack of pottasium caused by insufficient nourishment is rare.

In medical literature the lack of phosphate ions is deemed to be very rare. Some monographs [e.g. Knochel J. P.: Arch. Int. Med. 137, 203-220 (1977)] mention more than a hundred articles, which prove the lack of phosphate ion and the importance of hypophosphatemia in connection with completely different diseases. Knochel, J. P. mentions that the lack of magnesium, potassium and phosphate ions occurs in many cases simultaneously. He mentions later, that hypophosphatemia and the deficiency in phosphorus are rare conditions and are even more rare to be cured. [N. Eng. J. Med. Chem. 313, 447–449 (1985)].

Practically there are no prior art references concerning intracellularphosphorus deficiency. Therefore it has become a common view among practitioners that the only thing to be mentioned about phosphate ion is that we eat too much of it, thus we can speak about phosphate overfeedig (and not underfeeding) [see Selye H.: Amer. Heart H.: 55, 805–809 (1958) and Proc. Soc. Exp. Biol. Med. 98 580–583 (1958)]. And this can lead to the breakdown of the ion balance, which may cause diseases (Seelig, M.: Amer. J. Cardio. 63: 4G–21G, 1989).

Contrary to what was thought, I have found in my investigations that in spite of the sufficient or excessive phosphate intake the occurrence of the intracellular phosphate ion lack is similar to that of the intracellular magnesium lack. This is probably due to metabolic and energetic reasons. Consequently, any dose of phosphate ions is (or would be) added, the intracellular stability cannot be restored unless magnesium, potassium and zinc are also applied simultaneously. Thus we can improve the cellular metabolism and the ATP production (since this will finally lead to the normalization of the ion concentration).

The exclusive application of phosphate ions in an overdose damages the organism also because it may bind magnesium and zinc in the intestines by forming hardly soluble precipitates, and thus causing lack of said elements and developing diseases.

The aim of the invention is to produce a pharmaceutical composition comprising a combination of magnesium, zinc, phosphorus and potassium for regenerating cells. In most cases the effect of this composition on the sick organism is favourable (better than that of using the elements separately), and there are practically no side effects.

The invention is based on the recognition that if the appropriate magnesium, potassium and zinc supply is ensured, then the phosphorous ions do not hinder but promote the effect of these elements. Applying these elements simultaneously the effect is considerably better than applying any of them separately.

Consequently, the effect of a composition comprising Mg, Zn and K ions can be improved considerably by adding a mixture of $HPO_4^{2-}/H_2PO_4^-$ salts in an appropriate amount.

The invention is based on the recognition that a pharmaceutical composition containing zinc, magnesium, phosphorus and potassium in a certain ratio is effective for regenerating living cells. It could not be expected from the prior art that such a mixture produces a significant synergistic effect.

DISCLOSURE OF THE INVENTION

In accordance with the present invention, a novel method for the treatment of panic disorder is provided, comprising administration to a human patient in need of the same a novel pharmaceutical composition which comprises zinc, magnesium, phosphorus and potassium, wherein the weight ratio based on zinc, magnesium, phosphorus and potassium atoms is in the range of (1–15):(25–200):(50–200):(10.0–500), optionally in association with pharmaceutical carrier or excipient or additive.

The above elements (Zn, Mg, P, K) may be incorporated in the composition according to the invention in any form which is not toxic for the organism. Examples are chemical compounds, such as organic and inorganic compounds, chelates.

The elements may also be included on support such as ion exchanger, vegetable fibre, inert carrier with large specific surface, and the like. These supports are well known in the art.

Optionally the magnesium and potassium compounds may be selected from the phosphorus-containing magnesium and potassium compounds. The zinc, magnesium and potassium compound may preferably be selected from salts with organic or mineral acids. A mixture of these compounds can also be used.

Preferred zinc salts are for example zinc hydrogen aspartate [$Zn(AspH)_2$], zinc glutamate [$Zn(GluH)_2$], zinc sulfate ($ZnSO_4$) and the like.

Preferred magnesium salts are, among others, magnesium hydrogen aspartate [$Mg(AspH)_2$], magnesium glutamate [$Mg(GluH)_2$], magnesium hydrogen phosphate ($MgHPO_4$), magnesium hydrogen citrate (MgHCitrate), magnesium oxid (MgO) and like.

Among the potassium salts preferred are potassium dihydrogen phosphate ($KH_2PO_4$), dipotassium hydrogen phosphate ($K_2HPO_4$), potassium hydrogen aspartate (KHAsp), potassium hydrogen glutamate (KHGlu) and the like.

The phosphorus is preferably included in the composition in the form of a magnesium and/or potassium compound containing phosphorus.

Among the zinc salts the use of a salt with aspartic acid is particularly preferred.

Among the potassium salts dipotassium hydrogen phosphate and potassium dihydrogen phosphate are particularly preferred. In a particularly preferred embodiment of the invention the composition comprises

| | |
|---|---|
| 0,5–1,5% | by weight of zinc hydrogen aspartate |
| 30–60% | by weight of magnesium hydrogen aspartate |
| 15–30% | by weight of a 1:1 mixture of potassium dihydrogen phosphate and dipotassium hydrogen phosphate in association with a pharmaceutical carrier or excipient or additive |
| 8,5–54,4% | by weight of a carrier. |

When preparing the composition, the ingredients are mixed and formulated by methods well known in the art.

In most cases the effect of this composition on the sick organism is favourable (better than that of using the elements separately), and there are practically no side effects.

One hypothesis of the mechanism responsible for the advantageous results obtained by the present invention is as follows:

The composition according to the invention acts on the part of the cell metabolism which is similar in cells. The effect is not specific for a certain cell or tissue and not even for a species. The composition according to the invention promotes the restitution of sick cells i.e. it is cell regenerating. It tends to restore physiological intracellular and extracellular ion levels thus improving the damaged energy balance of the cells. Increasing the intracellular ATP concentration the intracellular ion milieu changes in the direction of normalization which improves ATP production and a "reversed vicious circle" develops. This may explain the often observed prompt improvement in the condition of the patients where the conventional medicaments had no effect. The regenerating effect of our composition does not develop if the damages of the sick cells are irreversible or strong noxious agent(s) is (are) permanently acting.

On the basis of our experiments on sick and healthy people, the composition according to the invention may be considered as a tonic or roborant which decreases the psychical tension and the muscle tonus in state of rest; has a positive effect on the physiological sleep and on the general physical condition.

Administered for prophylactic purposes, the composition according to the invention has a protective effect on cells against toxic influence or stress.

The composition according to the invention can be used alone but it can obviously be administered in combination with other medicaments. Namely, it reinforces their specific effect as a non specific tonic thus the dose of the medicaments can be decreased.

Also, the undesired and toxic side effects of certain medicaments can be diminished by the composition according to the invention. It is known namely, that toxic effects often decrease the ATP concentration and modify the intracellular ion concentrations. The daily doses of the composition of the invention are divided into ranges I to V.

Range I: For the purpose of prophylaxis and or maintaining improved conditions.

Range II: The usual daily doses.

Range III: For treating serious, obstinate cases. This range is also advised if magnesium and/or zinc is not contained in the composition in the form of a complex.

Range IV: Exceptional doses, usually applied only for a few days, if the seriousness of the disease makes in necessary.

Range V: Advised in case of incipient disorder of the kidneys. The sick kidneys must not be overburdened with potassium and phosphorus. In case of serious diseases of the kidneys the application of any form of the composition containing 4 minerals in contraindicated.

The advised daily doses:
Zinc: 0.03 to 1.5 mmoles (2 to 96 mg);
Magnesium: 2 to 100 mmoles (48 to 2400 mg);
Phosphorus: 2 to 60 mmoles (6.4 to 1860 mg);
Potassium: 3 to 90 mmoles (120 to 3500 mg).

|  | Zn | Mg | P | K |
| --- | --- | --- | --- | --- |
| Range I | 0.03–0.12 mmoles (2–8 mg) | 2–7 mmoles (48–170 mg) | 2–7 mmoles (64–220 mg) | 3.0–10.5 mmoles (120–410 mg) |
| Range II | 0.12–0.25 mmoles (8–16 mg) | 7–18 mmoles (170–430 mg) | 7–13 mmoles (220–400 mg) | 10.5–19 mmoles (410–740 mg) |
| Range III | 0.25–0.60 mmoles (2–8 mg) | 18–30 mmoles (430–720 mg) | 13–19 mmoles (400–620 mg) | 19–29 mmoles (740–1130 mg) |
| Range IV | 0.6–1.5 mmoles (38–96 mg) | 30–100 mmoles (720–2400 mg) | 19–60 mmoles (600–1860 mg) | 29–90 mmoles (1130–3500 mg) |
| Range V | 0.12–0.23 mmoles (7–15 mg) | 2–6 mmoles (50–150 mg) | 2.0 mmoles (60 mg) | 3.0 mmoles (120 mg) |

The administration of the pharmaceutical composition according to the invention can be via any of the accepted modes of administration such as oral and parenteral (i. v.)

Depending on the intended mode, the compositions according to the invention may be in the form of solid, semi-solid or liquid dosage forms, such, for example, as tablets, capsules, pills, powders, granules, crystals, liquids, suspensions, or the like. preferably in unit dosage forms suitable for administration of relatively precise dosage. The compositions may include a conventional pharmaceutical carrier or excipient.

For solid compositions the composition may include any conventional non-toxic solid carrier such as, for example, pharmaceutical grades of mannitol, lactose, starch; talcum, cellulose, glucose, sucrose, and the like.

Liquid pharmaceutical administrable compositions can, for example, be prepared by dissolving the mixture of the active ingredients in a carrier such as, for example, sterile water, aqueous dextrose, glycerol, and the like, to thereby form a solution or suspension.

Injectable solutions may be prepared in which the carrier comprises saline solution, glucose solution or a mixture thereof.

If desired, the pharmaceutical composition to be administered my also contain minor amount or non-toxic auxiliary substances such as acids to aid solubility, sweeteners and flavouring agents.

It is especially advantageous to formulate the composition according to the invention in dosage unit form for ease of administration and uniformity of dosage. Examples of such dosage unit forms are tablets (including packets, injectable solutions or suspensions, teespoonfuls, tablespoonfuls and the like, and segregated multiples thereof.

The following examples are intended to illustrate and not to limit the scope of the present invention. Unless otherwise stated all parts therein are by weight.

COMPOSITION EXAMPLES

Example 1: Tablets 1 part of $Zn(AspH)_2$, 25 part of $Mg(AspH)_2$, 15 part of $K_2HPO_4$, 10 part of $KH_2PO_4$ and 49 part of lactose are mixed well and compressed into tablets.

Example 2: Tablets 0.5 part of $Zn(GluH)_2$, 32 part of $Mg(GluH)_2$, 20 part of $K_2HPO_4$, 17 part of $KH_2PO_4$ and 30.5 part of lactose are mixed well and compressed into tablets.

Example 3: Tablets 1 part of $Zn(AspH)_2$, 44 part of $Mg(AspH)_2$, 3 part of $K_2HPO_4$, 2 part of $KH_2PO_4$ and 50 part of lactose are mixed well and compressed into tablets.

Example 4: Tablets 1 part of $Zn(AspH)_2$, 25 part of $MgHPO_4$, 40 part of $KH_2PO_4$ and 34 part of lactose are mixed well and compressed into tablets.

Example 5: Powder 3 part of $Zn(AspH)_2$, 70 part of $MgHPO_4$, 50 part of KHAsp are mixed well.

Example 6: Powder 5 part of $ZnSO_4.7H_2O$, 70 part of $MgHPO_4$, 50 part of KHGlu are mixed well.

Example 7: Powder 4 part of ZnHCitrate, 222 part of MgHCitrate, 66 part of $KH_2PO_4$, 84 part of $K_2HPO_4$ and 24 part of citric acid are mixed well.

Example 8: Powder 5 part of $Zn(AspH)_2$, 355 part of $Mg(AspH)_2$, 66 part of $KH_2PO_4$, 84 part of $K_2HPO_4$ and 10 part of polyvinyl-pyrrolidone are granulated and if desired compressed into tablets.

Example 9: Oral Solution 5 part of $Zn(AspH)_2$, 355 part of $Mg(AspH)_2$, 66 part of $KH_2PO_4$, 84 part of $K_2HPO_4$, 70 part of citric acid are dissolved in 6000 part of water.

Example 10: Oral Solution 5 part of $Zn(AspH)_2$, 355 part of $Mg(AspH)_2$, 66 part of $KH_2PO_4$, 84 part of $K_2HPO_4$, 100 part of ascorbic acid, 1 part aspartam (from Nutrasweet) and 1 part of of raspberry essence are dissolved in 6000 part of water.

Example 11: Capsules 5 part of $Zn(AspH)_2$, 355 part of $Mg(AspH)_2$, 66 part of $KH_2PO_4$, 84 part of $K_2HPO_4$ are vigorously stirred together. The resulting mixture is filled into suitable hardened gelatine capsules.

BIOLOGICAL EXAMPLE

Example 12: Anxiety Neurosis/Panic Disorder 12 patients suffering from anxiety neurosis (synonym: panic disorder) were administered perorally 4, 5–6 g/day of the composition according to Example 8, for 7 to 14 days. The main symptoms were: palpitation, breathlessness, morning asthenia, anxiety, headache, paraesthesias, dizziness. Their symptoms had been nearly stable for 1 to 12 months and were not relieved by beta-blocking agents or/and sedatives. After administering the medicine according to the invention 5 patients became free of symptoms, 6 were improved significantly, only one patient's symptoms did not change.

TABLE 3

|  | free of symptoms | improved | unchanged |
|---|---|---|---|
| Anxiety neurosis | 5 | 6 | 1 |

I claim:

1. A method for treating panic disorder, which comprises administering to a human suffering from panic disorder 0.03 to 1.5 mmoles of zinc and 2 to 100 mmoles of magnesium and 2 to 60 mmoles of phosphorus and 3 to 90 mmoles of potassium as a daily dose in a composition consisting essentially of zinc, magnesium, phosphorus and potassium, in a weight ratio of 1–15:25–200:50–200:100–500, respectively.

* * * * *